(12) United States Patent
Wang et al.

(10) Patent No.: US 8,703,193 B2
(45) Date of Patent: Apr. 22, 2014

(54) CONTROLLED POROUS OSMOTIC PUMP TABLETS OF HIGH PERMEABLE DRUGS AND THE PREPARATION PROCESS THEREOF

(75) Inventors: Jingang Wang, Beijing (CN); Haisong Jiang, Haerbin (CN)

(73) Assignee: Cosci Med-Tech Co. Ltd., Beijing (CN)

( * ) Notice: Subject to any disclaimer, the term of this patent is extended or adjusted under 35 U.S.C. 154(b) by 161 days.

(21) Appl. No.: 12/445,690

(22) PCT Filed: Oct. 16, 2007

(86) PCT No.: PCT/CN2007/002967
§ 371 (c)(1),
(2), (4) Date: Jul. 15, 2009

(87) PCT Pub. No.: WO2008/052417
PCT Pub. Date: May 8, 2008

(65) Prior Publication Data
US 2010/0291208 A1 Nov. 18, 2010

(30) Foreign Application Priority Data
Oct. 16, 2006 (CN) .......................... 2006 1 0140521

(51) Int. Cl.
A61K 31/137 (2006.01)
A61K 9/24 (2006.01)
A61K 31/138 (2006.01)

(52) U.S. Cl.
USPC ............ 424/473; 514/523; 514/653; 514/651

(58) Field of Classification Search
USPC .......................... 424/473; 514/523, 653, 651
See application file for complete search history.

(56) References Cited

U.S. PATENT DOCUMENTS

| 2,799,241 | A | * | 7/1957 | Wurster | .......................... 118/24 |
| 6,004,582 | A | * | 12/1999 | Faour et al. | ................... 424/473 |
| 6,046,177 | A | | 4/2000 | Stella et al. | |
| 2005/0008702 | A1 | | 1/2005 | Faour et al. | |
| 2005/0163851 | A1 | * | 7/2005 | Feleder et al. | ................. 424/473 |

FOREIGN PATENT DOCUMENTS

| CN | 1771921 A | 5/2006 |
| CN | 1923184 A | 3/2007 |
| WO | WO 00/41704 | 7/2000 |

OTHER PUBLICATIONS

He Li-L1, et al., "Effects of coating on the in vitro release character of sodium ferulate controlled porosity osmotic pump tablets," West China Journal of Pharmaceutical Sciences, Jun. 2006, vol. 21:3; pp. 218-222, ISSN 1006-0103.

S. N. Makhija et al., "Controlled porosity osmotic pump-based controlled release systems of pseudoephedrine: I. Cellulose acetate as a semipermeable membrane," Journal of Controlled Release, 2003, vol. 89, pp. 5-18, ISSN 0168-3659.

G. M. Zentner et al., "Osmotic Flow Through Controlled Porosity Films: An Approach to Delivery of Water Soluble Compounds," Journal of Controlled Release, 1985, vol. 2, pp. 217-229, ISSN 0168-3659.

European Patent Office supplementary search report on application No. 07816581.8 dated Sep. 20, 2011; 5 pages.

* cited by examiner

Primary Examiner — Anoop Singh
Assistant Examiner — Anna Falkowitz
(74) Attorney, Agent, or Firm — Foley & Lardner LLP

(57) ABSTRACT

The present invention relates to controlled porous osmotic pump tablets of high permeable drugs and the preparation process thereof. The controlled porosity osmotic pump tablets do not need to be drilled by laser, but provides controlled porosity for drug release by adding a suitable quantity of pore-forming agents into the semipermeable membrane. In specific embodiments, the present invention relates to controlled porous osmotic pump tablets comprising venlafaxine or metoprolol or pharmaceutically acceptable salts thereof.

24 Claims, 2 Drawing Sheets

CONTROLLED POROUS OSMOTIC PUMP TABLETS OF HIGH PERMEABLE DRUGS AND THE PREPARATION PROCESS THEREOF

This application is the National Phase of PCT/CN2007/002967, filed Oct. 16, 2007, which claims priority to Chinese Application No. 200610140521.2, filed Oct. 16, 2006. The contents of the foregoing applications are incorporated herein by reference in their entirety.

TECHNICAL FIELD

The present invention relates to controlled porous osmotic pump tablets of high permeable drugs and the preparation process thereof. The controlled porosity osmotic pump tablets do not need to be drilled by laser, but provides controlled porosity for drug release by adding a suitable quantity of pore-forming agents into the semipermeable membrane. This not only simplifies the preparation process, and greatly reduces the production cost, but also increases the safety of the preparation. In specific embodiments, the present invention relates to controlled porous osmotic pump tablets comprising venlafaxine or metoprolol or pharmaceutically acceptable salts thereof.

BACKGROUND OF THE ART

In 1955, two Australian scholars, Rose and Nelson, developed an osmotic pump for administration to livestocks. In 1970's, the osmotic pump was simplified by Alza Co. In 1974, Theeuwes developed a single-chamber osmotic pump, which was in a simple form of ordinary coated tablet with one side being drilled. Thus, osmotic pump became a dosage form that could be used in clinic, and therefore a series of single-chamber controlled osmotic pump tablets dosage forms were developed. From 1980's, the modification and development about osmotic pump never stopped. In order to prepare insoluble drug into osmotic pump, or to prepare drug with good water solubility but cannot produce osmotic pressure by itself into osmotic pump, a single-chamber bilayer osmotic pump was developed. In order to release drug stably, a double-chamber osmotic pump was developed. In order to be adapted to circadian rhythm of human body, a timed-release osmotic pump was developed, and so on.

A series of defects exist in the preparation of controlled osmotic pump tablets by laser drilling process, for example, (1) a high cost: a device for laser drilling costs above one million Yuan; moreover, an usual carbon dioxide laser device can only generate excitation for $5 \times 10^5$ times in its service life, if one tablet is drilled once, one laser tube can only be used to produce 2 to 3 batches of drugs; the cost and maintenance charge of the device are quite expensive; (2) a low yield and a great labor intensity: laser drilling inevitably has the problems of missed drilling (in the case of the tablets being not tightly caught by a collector and falling off), over drilling (in the case of the tablets being not cleared away from the drilling place by a sweeper in time), depth of drilling being insufficient (in the case of reduced laser energy) to penetrate the semipermeable membrane, wrong drilling position, and etc., thus a relatively low yield is resulted. Since there isn't a process now to automatically screen out unqualified osmotic pumps, the tablets having the problems of missed drilling, over drilling, wrong drilling position and insufficient depth of drilling must be screened out manually during the production. This is a job that quite consumes time and involves a great effort. In general, one batch of samples includes $2 \times 10^5$ tablets, and the job of manually screening out unqualified tablets needs 7 days to be accomplished, which involves quite high labor intensity.

Although the design of osmotic pump is very ingenious, various shortcomings, for example, too many procedures involved in the industrialized production thereof, strict requirements on the indexes of controlling each procedure, great difficulty involved in the production, long production period, high cost, and high rate of rejects, seriously restrict the extension of osmotic pump product. As can be seen from the development course of osmotic pump, the industrialization of osmotic pump is accelerated by each time of simplification on the structure and process of osmotic pump, thus the development of osmotic pump having simple structure, low difficulty in industrialized production, and low production cost is an important tendency in the field.

DESCRIPTION OF THE INVENTION

The object of the present invention is to provide controlled porous osmotic pump tablets which do not need to be drilled by laser and the preparation process thereof. This invention not only simplifies the preparation process, and greatly reduces the production cost, but also increases the safety of the preparation.

In order to achieve the above object, the present invention adopts the following technical solution:

A controlled porous osmotic pump tablet, which comprises a core and a semipermeable membrane, wherein the core comprises a principal agent, a permeation enhancer and a permeation aid, and the semipermeable membrane comprises a film-forming material and a pore-forming agent; if necessary, the semipermeable membrane may be further coated with a thin film that comprises a conventional film material that is commonly used in the field of tablets. The semipermeable membrane comprises the pore-forming agent in an amount of 20-45%, preferably 25-35%, by weight of the semipermeable membrane. The semipermeable membrane is present in an amount of 10-35%, preferably 20-30%, by weight of the core. The thin film is preferably present in an amount of 3-6% by weight of the tablet.

As for the above-mentioned controlled porous osmotic pump tablets, the pore-forming agent therein is selected from the group consisting of polyethylene glycol (having a molecular weight of 2000-6000), hydroxypropyl cellulose, micronized sugar, sodium chloride, mannitol, sorbitol, and mixtures thereof, preferably polyethylene glycol.

The principal agent used herein includes drugs having good water solubility and quite strong permeability. In practice, the inventor discovered that, when the principal agent per se had good water solubility and quite strong permeability, the drug could be completely released though a semipermeable membrane in the case of no drilling with laser. The present invention fully utilizes the solubility and permeability of the drug per se, and, by an ideal combination of good water solubility and permeability of the drug per se, prepares a controlled porous osmotic pump tablet that does not need to be drilled with laser, and thereby saves a lot of investment, greatly reduces labor intensity, and increases the safety of the drug. In specific embodiments of the present invention, venlafaxine and metoprolol or pharmaceutically acceptable salts thereof are preferred, and venlafaxine hydrochloride and metoprolol tartrate are especially preferred.

As for the above-mentioned controlled porous osmotic pump tablets, the fill-forming material in the semipermeable membrane is selected from the group consisting of cellulose acetate, ethyl cellulose, hydroxypropylmethyl cellulose, polyacrylic resin, and mixtures thereof, preferably cellulose acetate.

As for the above-mentioned controlled porous osmotic pump tablets, the permeation enhancer is selected from the group consisting of sodium chloride, potassium chloride, mannitol, lactose, sorbitol, and mixtures thereof, preferably sodium chloride or mannitol.

As for the above-mentioned controlled porous osmotic pump tablets, the semipermeable membrane may further comprise a plasticizer selected from the group consisting of triethyl citrate, dibutyl sebacate, phthalates, polyethylene glycol 4000, and mixtures thereof, preferably dibutyl sebacate.

As for the above-mentioned controlled porous osmotic pump tablets, the permeation aid in the core is selected from the group consisting of microcrystalline cellulose, lactose, alginic acid, alginate, propylene glycol alginate, polyethylene glycol, and mixtures thereof, preferably microcrystalline cellulose, alginic acid or propylene glycol alginate.

As for the above-mentioned controlled porous osmotic pump tablets, the core may further comprise a lubricant selected from the group consisting of magnesium stearate, calcium stearate, zinc stearate, glyceryl monostearate, sodium stearyl fumarate, polyoxyethylene monostearate, sucrose monolaurate, sodium lauryl sulfate, magnesium lauryl sulfate, magnesium dodecyl sulfate, saponite, and mixtures thereof, preferably magnesium stearate.

In the course of preparing the core, the materials in mixture may be granulated by a wet process or a dry process. In the wet process, water or anhydrous ethanol, isopropanol, ethanol, a mixture of ethanol or isopropanol and water is used as a binder.

As for the above-mentioned auxiliary materials such as permeation enhancer, permeation aid, film-forming material, plasticizer and lubricant, they may be suitably selected according to the releasing effect and the property and concrete use of the drug, and etc. After reading the content described in the present invention, a person skilled in the art could determine their suitable amounts by conventional experimentation.

In one specific embodiment of the present invention, the controlled porous osmotic pump tablets, if desired, may further comprise a thin film coated on the semipermeable membrane, and alternatively, the thin film may further comprise a principal agent. By using a pharmaceutically conventional film material, for example, a film-forming material such as low-viscosity hydroxypropylmethyl cellulose and polyacrylic resin, a plasticizer such as triethyl citrate, dibutyl sebacate, phthalates and polyethylene glycol 4000, a thin film comprising a principal agent is coated on the semipermeable membrane by a conventional film coating technique, to provide a drug for quick release, and thereby achieve a rapid curative effect.

Furthermore, the present invention provides a process for preparing the above-mentioned controlled porous osmotic pump tablets, which comprises the steps of: (1) mixing a principal agent and auxiliary materials for the core, granulating, and tabletting to prepare the core; (2) formulating the materials for the semipermeable membrane with acetone, ethanol or isopropanol (preferably 90% isopropanol) to obtain a coating solution, placing the core prepared in step (1) in a coating machine, coating the core with the coating solution until the semipermeable membrane accounts for 10-35% by weight of the core, then taking out the coated tablets and volatizing the solvent till dryness. In one preferred embodiment, when coating the semipermeable membrane, the air temperature at the outlet is controlled below 25° C., the air temperature at the inlet is controlled below 35° C., and the material temperature is controlled between 25 and 30° C.

If desired, the above-mentioned process may further comprise a step of placing the semipermeable membrane-coated tablets prepared in step (2) in a coating machine, and coating it with a thin film coating solution, to thereby obtain a controlled porous osmotic pump tablets which further comprises a principal agent-comprising thin film on the semipermeable membrane. The principal agent-comprising thin film, by weight percents, preferably comprises 20-40% of a principal agent, 50-80% of a film-forming material, and 5-10% of a plasticizer. Moreover, the quantity of principal agent in the principal agent-comprising thin film is 10-20% of the quantity of principal agent in the core.

In one specific embodiment of the present invention, the principal agent is preferably venlafaxine, metoprolol or pharmaceutically acceptable salts thereof, particularly preferably venlafaxine hydrochloride and metoprolol tartrate.

Venlafaxine hydrochloride has a chemical name: (±)-1-[2-(dimethylamino)-1-(4-methoxyphenyl)ethyl]cyclohexanol hydrochloride, and is expressed by the following formula:

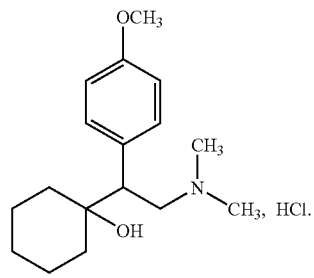

Venlafaxine is 5-hydroxytryptamine (5-HT)-norepinephrine (NE) re-uptake inhibitor, and takes antidepressant effect by remarkably inhibiting the re-uptake of 5-HT and NE. Venlafaxine can enhance the activity of certain neurotransmitters in human neutral nervous system. Venlafaxine and its active metabolite O-desmethylvenlafaxine (ODV) can effectively inhibit the re-uptake of 5-HT and NE, and also take a certain inhibitory effect on the re-uptake of dopamine. This drug is applicable to various kinds of depressions, including depression accompanied with anxiety, and universal anxiety disorders.

The initial recommended dose of venlafaxine in clinic is 75 mg/day, once per day, and, if necessary, said dose may be gradually increased up to 225 mg/day (by an increase of 75 mg/day once, in a time interval of not less than 4 days). The initial dose for patients with liver dysfunction is reduced by 50%, and dose individuation is required for certain patients. The total dose administered each day to the patients with kidney dysfunction is reduced by 25-50%. The administration to senile patients is performed individually, and special attention shall be paid when the dose administered thereto is increased.

As one of the embodiments of the above-mentioned controlled porous osmotic pump tablets, the present invention provides controlled porous osmotic pump tablets of venlafaxine hydrochloride, consisting of a core, a semipermeable membrane and optionally a principal agent-comprising thin film coated on the semipermeable membrane, wherein the core comprises, by weight percents, 25-50% of venlafaxine hydrochloride, 10-35% of a permeation enhancer, 20-40% of a permeation aid and 0.5-1% of a lubricant, the semipermeable membrane comprises, by weight percents, 50-70% of a film-forming material, 20-45% of a pore-forming agent and 3-10% of a plasticizer, and the semipermeable membrane is present in an amount of 10-35% by weight of the core; if the tablet further comprises a principal agent-comprising thin film, the principal agent-comprising thin film comprises, by weight percents, 20-40% of venlafaxine hydrochloride, 50-80% of a film-forming material, and 5-10% of a plasticizer, and the weight of venlafaxine hydrochloride in the principal agent-comprising thin film is 10-20% of the weight of venlafaxine hydrochloride in the core.

In one specific embodiment of the above-mentioned controlled porous osmotic pump tablet of venlafaxine, the core comprises venlafaxine hydrochloride, microcrystalline cellulose, sodium chloride and magnesium stearate, the semipermeable membrane comprises cellulose acetate, polyethylene glycol (6000) and dibutyl sebacate, and the optional principal agent-comprising thin film comprises venlafaxine hydrochloride, hydroxypropylmethyl cellulose and polyethylene glycol (4000); and the tablets are prepared by a process comprising the steps of: (1) preparation of the core—uniformly mixing venlafaxine hydrochloride, sodium chloride and a part of microcrystalline cellulose, granulating the resultant mixture, uniformly mixing the resultant granules with the remaining microcrystalline cellulose and magnesium stearate, and tableting; (2) coating of the core—dissolving cellulose acetate, polyethylene glycol 6000 and dibutyl sebacate with a suitable solvent to obtain a coating solution, placing the core prepared in step (1) in a coating machine, coating the core with the coating solution, then taking out the coated tablets and volatizing the solvent till dryness; (3) optional coating of the coated tablets with a principal agent-comprising thin film—dissolving venlafaxine hydrochloride, hydroxypropylmethyl cellulose and polyethylene glycol 4000 with a suitable solvent to obtain a principal agent-comprising thin film coating solution, placing the coated tablets obtained in step (2) in a coating machine, coating it with the principal agent-comprising thin film coating solution, then taking out the coated tablets and volatizing the solvent till dryness.

As another embodiment of the above-mentioned controlled porous osmotic pump tablets, the present invention provides controlled porous osmotic pump tablets of metoprolol, particularly controlled porous osmotic pump tablets of metoprolol tartrate. Metoprolol tartrate has a chemical name: 1-isopropylamino-3[p-(2-methoxyethyl)phenoxy]-2-propanol L(+)-tartrate, and is expressed by the following formula:

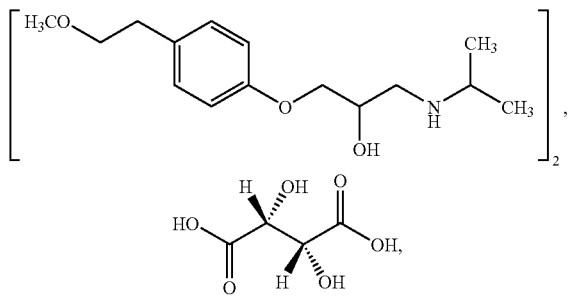

Molecular formula: $(C_{15}H_{25}NO_3)_2 \cdot C_4H_6O_6$, molecular weight: 684.82.

Metoprolol tartrate is beta1-adrenoceptor blocking drug (cardioselective beta-adrenoceptor blocking drug) of 2A type, i.e., without partial agonist activity. It exhibits selective blocking effect to beta1-adrenoceptor, without PAA (partial agonist activity), and without membrane-stabilizing action. The effects of metoprolol on heart, such as slowing heart rate, inhibiting cardiac contraction force, lowering autorhythmicity and delaying atrioventricular conduction time, are similar to those of propranolol (PP) and atenolol (AT), so are the effects thereof for reducing increased blood pressure and heart rate in exercise test. This drug is suitable for the treatment of hypertension, angina pectoris, and etc.

Metoprolol tartrate is a new kind of safe and effective adrenoceptor blocking agent, and has a definite curative effect of reducing pressure. It has the effect of slowing heart rate, can effectively reduce blood pressure and heart rate in active sports, and can also correspondingly enhance the symptoms such as headache, chest distress and cardiopalmus. The influence on heart rate has no obvious difference between two-week administration and four-week administration. The drug can obviously reduce renal vascular resistance, and a long-term administration of the drug has protective action on heart and kidney. It can be used as an ideal pressure-reducing drug.

As another embodiment of the above-mentioned controlled porous osmotic pump tablets, the present invention provides a controlled porous osmotic pump tablet of metoprolol tartrate, consisting of a core and a semipermeable membrane, wherein the core comprises, by weight percents, 12-25% of metoprolol tartrate, 10-65% of a permeation enhancer, 15-40% of a permeation aid and 0.5-1% of a lubricant, the semipermeable membrane comprises, by weight percents, 50-70% of a film-forming material, 20-45% of a pore-forming agent and 3-10% of a plasticizer, and the semipermeable membrane is present in an amount of 10-35% by weight of the core.

It is surprisingly found in the present invention that the controlled porous osmotic pump tablets of the present invention do not need to be drilled, but forms continuous pores for drug release by using a relatively large quantity of pore-forming agents, to thereby avoid a series of defects associated with the preparation of a controlled osmotic pump by laser drilling process.

As compared with the existing osmotic pump, the controlled porous osmotic pump tablets of the present invention have prominent advantages, for example:

(1) No need of drilling with laser, reduced cost: since the producer does not need to purchase expensive laser drilling device, and does not need to frequently change vulnerable laser tube, and can produce controlled release tablets having good releasing effect by using conventional taletting device and coating device, the cost of device is greatly reduced.

(2) Simplified process, reduced labor intensity, and increased reliability of process: since the two procedures of drilling with laser and manually screening are omitted, the process becomes relatively simple, and accordingly the reliability and stability of the process are increased. In the production, the occurrence probability of unqualified products due to incorrect control of procedures in the process is greatly reduced.

(3) Increased safety of preparation: drug is released through multiple pores, which is safer than the release of drug through a single pore drilled with laser; once the controlled porous osmotic pump tablet meets digestive juice when entering into human body, the pore-forming agent automatically generates pores, while the problems including missed drilling, over drilling, insufficient depth of drilling and wrong drilling position associated with the use of a laser device will not occur, and the problem such as invalidation due to blockage of the single pore with foods or sudden release will not occur as well, so that the safety is greatly increased.

EMBODIMENTS OF THE INVENTION

The content of the present invention is further explained or illustrated by the following examples. The examples only help to understand the content of the present invention, and should not be understood to limit the gist and protection scope of the present invention.

The release rate herein is determined according to process 1 in Appendix XD of Chinese Pharmacopoeia (2005 Edition) Volume II, with water as release medium.

EXAMPLE 1

Composition of Core

| Venlafaxine hydrochloride | 75 g |
| Microcrystalline cellulose | 45 g |
| Sodium chloride (NaCl) | 35 g |
| Magnesium stearate | 1 g |

Composition of Semipermeable Membrane:

| Cellulose acetate | 21 g |
| Polyethylene glycol 6000 | 9 g |
| Dibutyl sebacate | 2 g |

1000 tablets were prepared according to the following process:

(1) Preparation of Core:

Sodium chloride (−100 meshes) was uniformly mixed with venlafaxine hydrochloride and microcrystalline cellulose, to which ethanol was added as a wetting agent to obtain a soft material; the soft material passed through a 30-mesh sieve, granulated, and dried at 45° C. for 2 hours; the obtained granules were screened and uniformly mixed with magnesium stearate, and then tabletted with a conventional tabletting technique to obtain 1000 tablets.

(2) Coating of the Core:

Cellulose acetate was dissolved by 600 ml acetone with stirring; in a 50 ml measuring flask, polyethylene glycol was dissolved with water, the obtained solution was added to the 1500 ml acetone solution of cellulose acetate as above obtained with stirring, to fully dissolve polyethylene glycol, and then dibutyl sebacate was added with shaking, to obtain a coating solution. The core as above prepared was placed in a coating machine, to which a hot air was charged, and the coating solution was sprayed onto the core while keeping the temperature between 30 and 40° C. Finally, the coated tablets were placed in an environment of 40° C. to vaporize the solvent to dryness.

Figure 1:
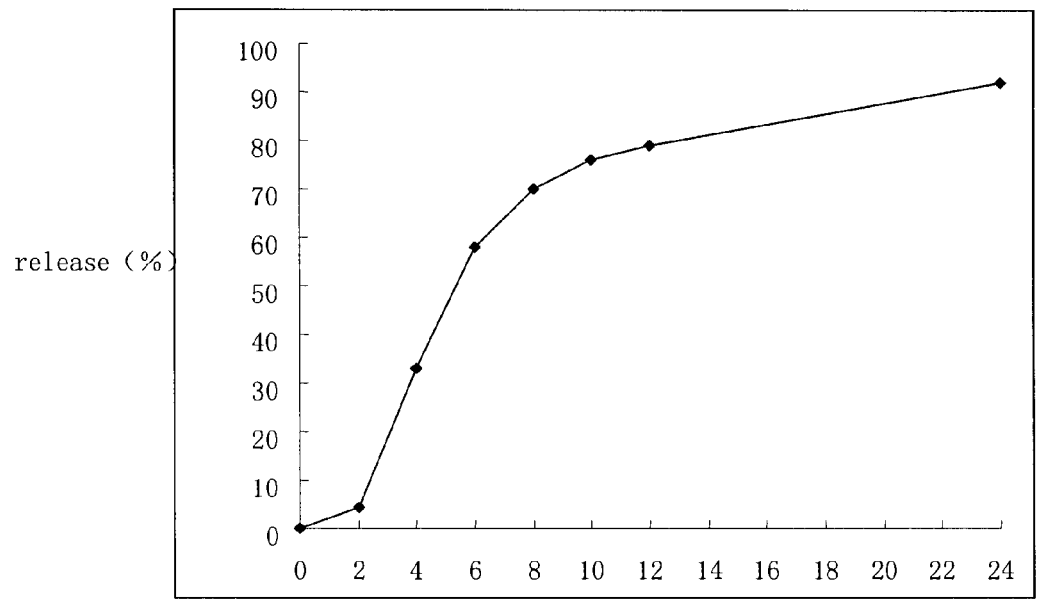
FIG. 1: Accumulated release curve of Example 1.

The release rate of the tablets was determined according to process 1 in Appendix XD of Chinese Pharmacopoeia (2000 Edition) Volume II, with the results listed as follows: 4% of drug was released at 2 hours; 31% at 4 hours; 70% at 8 hours; 81% at 12 hours; 93% at 24 hours. The accumulated release curve was shown in FIG. 1.

Example 2

Composition of Core

| Venlafaxine hydrochloride | 75 g |
| Alginic acid | 30 g |
| Propylene glycol alginate | 20 g |
| Mannitol | 30 g |
| Magnesium stearate | 2 g |

Composition of Semipermeable Membrane:

| Polyacrylic resin | 5 g |
| Ethyl cellulose | 14 g |
| Hydroxypropyl cellulose | 6 g |
| Triethyl citrate | 2 g |

1000 tablets were prepared according to the following process:

(1) Preparation of Core:

Mannitol (−100 meshes) was uniformly mixed with venlafaxine hydrochloride, alginic acid and propylene glycol alginate, to which ethanol was added as a wetting agent to obtain a soft material; the soft material passed through a 30-mesh sieve, granulated, and dried at 45° C. for 2 hours; the obtained granules were screened and uniformly mixed with magnesium stearate, and then tabletted with a conventional tabletting technique to obtain 1000 tablets.

(2) Coating of the Core:

Polyacrylic resin, ethyl cellulose and hydroxypropyl cellulose were dissolved by 1500 ml ethanol with stirring, to which triethyl citrate was added with shaking, to obtain a coating solution. The core as above prepared was placed in a coating machine, to which a hot air was charged, and the coating solution was sprayed onto the core while keeping the temperature between 30 and 40° C. Finally, the coated tablets were placed in an environment of 40° C. to vaporize the solvent to dryness.

Figure 2:
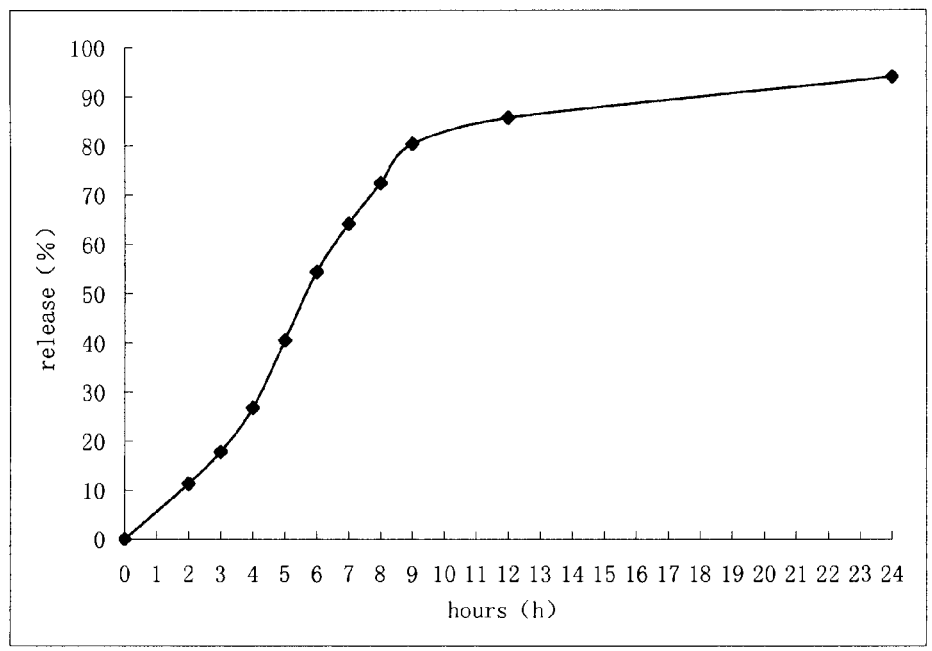
FIG. 2: Accumulated release curve of Example 2.

The release rate of the tablets were determined according to process 1 in Appendix XD of Chinese Pharmacopoeia (2000 Edition) Volume II, with the results listed as follows: 11% of drug was released at 2 hours; 27% at 4 hours; 72% at 8 hours; 86% at 12 hours; 93% at 24 hours. The accumulated release curve was shown in FIG. 2.

Example 3

Composition of Core

| Venlafaxine hydrochloride | 75 g |
| Microcrystalline cellulose | 60 g |
| Sodium chloride | 40 g |
| Magnesium stearate | 0.9 g |

Composition of Semipermeable Membrane:

| Cellulose acetate | 25 g |
|---|---|
| Polyethylene glycol (6000) | 11 g |
| Dibutyl sebacate | 2.5 g |

Composition of Principal Agent-Comprising Thin Film

| Venlafaxine | 10 g |
|---|---|
| Hydroxypropylmethyl cellulose | 20 g |
| Polyethylene glycol (4000) | 2 g |

1000 tablets were prepared according to the following process:

(1) Preparation of Core:

Put sodium chloride for use. 75 g venlafaxine hydrochloride, 30 g microcrystalline cellulose and 40 g sodium chloride passed through a 60-mesh sieve, and were uniformly mixed. A 10% polyvinylpyrrolidone k-30 ethanol solution was added in a suitable amount to the resultant mixture, to obtain a soft material; the soft material passed through a 30-mesh sieve, granulated, and dried in a dryer at 40° C. the obtained granules were uniformly mixed with the remaining microcrystalline cellulose and magnesium stearate, and then tabletted with a conventional tabletting technique to obtain 1000 tablets.

(2) Coating of the Core with a Semipermeable Membrane:

Cellulose acetate was dissolved by a suitable amount of acetone; polyethylene glycol 6000 was dissolved with a suitable amount of water, the obtained solution was slowly added to the acetone solution of cellulose acetate as above obtained, and then dibutyl sebacate was dissolved therein, to obtain a coating solution.

The core as above prepared was placed in a coating machine, to which a hot air was charged, and the coating solution was sprayed onto the core while keeping the temperature between 30 and 40° C. Finally, the coated tablets were placed in an environment of 40° C. to vaporize the solvent to dryness.

(3) Coating of the Coated Tablets with a Principal Agent-Comprising Thin Film:

Hydroxypropylmethyl cellulose was dissolved with a suitable amount of 70% ethanol, and then venlafaxine hydrochloride and polyethylene glycol (4000) were dissolved therein, to obtain a coating solution of a principal agent-comprising thin film.

The coated tablets as above prepared were placed in a coating machine, to which a hot air was charged, and the coating solution of a principal agent-comprising thin film as above obtained was sprayed onto the coated tablets while keeping the temperature between 30 and 35° C. Finally, the coated tablets were placed in an environment of 40° C. to vaporize the solvent to dryness.

Figure 3:
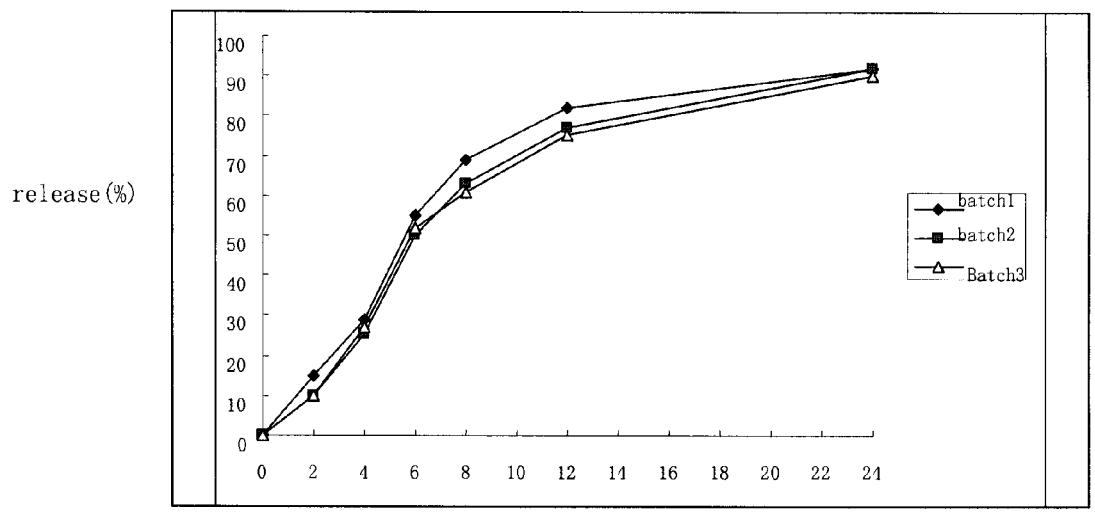
FIG. 3: Accumulated release curve of Example 3.

Three batches of products were prepared according to the above process. The release rates of the tablets were determined according to process 1 in Appendix XD of Chinese Pharmacopoeia (2000 Edition) Volume II, with the results listed as follows: 10-15% of drug was released at 2 hours; 25-30% at 4 hours; 50-55% at 6 hours; 60-70% at 8 hours; 75-85% at 12 hours; 90-95% at 24 hours. The accumulated release curve was shown in FIG. 3.

The above experiments also indicated that the process for preparing the controlled porous osmotic pump tablets had good maneuverability, and good repeatability.

Example 4

Composition of Core

| Metoprolol tartrate | 50.0 g |
|---|---|
| Microcrystalline cellulose | 50.0 g |
| Lactose | 147.5 g |
| Magnesium stearate | 2.5 g |

Composition of Semipermeable Membrane:

| Cellulose acetate | 35 g |
|---|---|
| Polyethylene glycol (PEG) 6000 | 12 g |
| Dibutyl sebacate | 3.5 g |
| Acetone | 837 g |
| Water | 30 g |

1000 Tablets were prepared according to the following process:

Preparation of binder: 10 g 95% ethanol and 10 g water was uniformly mixed to obtain a 50% ethanol solution. Preparation of a semipermeable membrane coating solution: cellulose acetate of the prescribed amount was dissolved with a suitable amount of acetone to formulate a 4% (g/g) acetone solution of cellulose acetate; PEG 6000 of the prescribed amount was slowly added in water with continuous stirring, to formulate a 27.8% aqueous solution of PEG 6000 (g/g); the aqueous solution of PEG 6000 was slowly added to the acetone solution of cellulose acetate with continuous stirring to obtain a homogenous solution; dibutyl sebacate of the prescribed amount was slowly added to the solution with stirring, to obtain a coating solution.

Metoprolol tartrate and lactose of the prescribed amounts passed through a 80-mesh sieve and uniformly mixed, microcrystalline cellulose was uniformly mixed therein, and then a suitable amount (about 20 g) of the binder was added to the resultant mixture, followed by granulating; the obtained granules passed through a 20-mesh sieve, and dried at 50° C. till a moisture content below 1%. The dried granules passed through a 20-mesh sieve, and then uniformly mixed with magnesium stearate of the prescribed amount; the resultant mixture was tabletted with a 9# shallow concave with a hardness of 8 kg. The weight of the resultant tablets was increased by 20% after coating.

Figure 4:
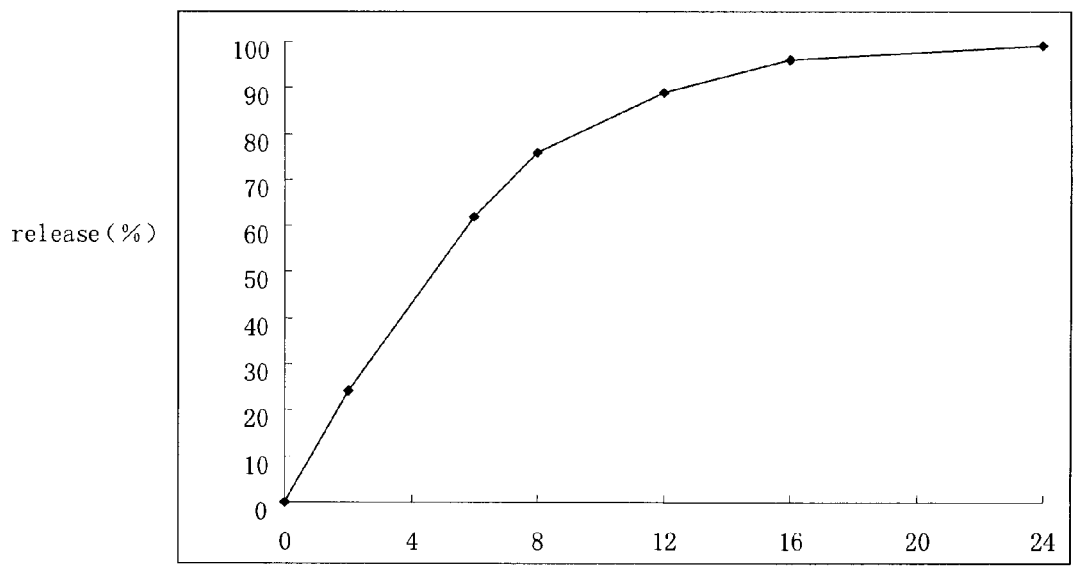
FIG. 4: Accumulated release curve of Example 4.

The release rate of the tablets was determined according to process 1 in Appendix XD of Chinese Pharmacopoeia (2000 Edition) Volume II, with the results listed as follows: 22% of drug was released at 2 hours; 62% at 6 hours; 76% at 8 hours; 89% at 12 hours; 92% at 24 hours. The accumulated release curve was shown in FIG. 4.

The present invention is described in detail by the above examples. It should be indicated that the above examples are only for exemplifying the present invention. On the premise of not departing from the spirit and essence of the present invention, a person skilled in the art may design many alternative solutions and ameliorated solutions of the present invention, which should be, without exception, understood to be in the protection scope of the present invention.

The invention claimed is:
1. A controlled porous osmotic pump tablet without being drilled by using laser comprising:
   (a) a core comprising a principal agent, a permeation enhancer and a permeation aid;
   (b) a semipermeable membrane disposed over the core, the semipermeable membrane comprising pores and comprising a film-forming material and a pore-forming agent forming the pores of the semipermeable membrane;
   wherein the semipermeable membrane comprises 20-45% by weight of the pore-forming agent, said pore-forming agent is selected from the group consisting of polyethylene glycol 2000-6000, hydroxypropyl cellulose, or both, and the film-forming material is selected from the group consisting of cellulose acetate, ethyl cellulose, hydroxypropylmethyl cellulose, polyacrylic resin, and mixtures thereof; and
   wherein the semipermeable membrane is present in an amount of 10-35% by weight of the core.

2. The controlled porous osmotic pump tablet according to claim 1, wherein the semipermeable membrane comprises 25-35% by weight of the pore-forming agent.

3. The controlled porous osmotic pump tablet according to claim 1, wherein the semipermeable membrane is present in an amount of 20-30% by weight of the core.

4. The controlled porous osmotic pump tablet according to claim 1, wherein the semipermeable membrane is further coated with a conventional thin film.

5. The controlled porous osmotic pump tablet according to claim 1, wherein the principal agent is venlafaxine hydrochloride or metoprolol tartrate.

6. The controlled porous osmotic pump tablet according to claim 1, wherein the film-forming material comprises cellulose acetate.

7. The controlled porous osmotic pump tablet according to claim 1, wherein the permeation enhancer is selected from the group consisting of sodium chloride, potassium chloride, mannitol, lactose, sorbitol, and mixtures thereof.

8. The controlled porous osmotic pump tablet according to claim 7, wherein the permeation enhancer comprises sodium chloride, mannitol, or both.

9. The controlled porous osmotic pump tablet according to claim 1, wherein the semipermeable membrane further comprises a plasticizer.

10. The controlled porous osmotic pump tablet according to claim 9, wherein the plasticizer is selected from the group consisting of triethyl citrate, dibutyl sebacate, phthalates, polyethylene glycol 4000, and mixtures thereof.

11. The controlled porous osmotic pump tablet according to claim 1, wherein the plasticizer comprises dibutyl sebacate.

12. The controlled porous osmotic pump tablet according to claim 1, wherein the permeation aid is selected from the group consisting of microcrystalline cellulose, lactose, alginic acid, alginate, propylene glycol alginate, polyethylene glycol, and mixtures thereof.

13. The controlled porous osmotic pump tablet according to claim 12, wherein the permeation aid comprises microcrystalline cellulose, alginic acid, propylene glycol alginate, or a combination thereof.

14. The controlled porous osmotic pump tablet according to claim 1, wherein the core further comprises a lubricant.

15. The controlled porous osmotic pump tablet according to claim 14, wherein the lubricant is selected from the group consisting of magnesium stearate, calcium stearate, zinc stearate, glyceryl monosterate, sodium stearyl fumarate, polyoxyethylene monostearate, sucrose monolaurate, sodium lauryl sulfate, magnesium lauryl sulfate, magnesium dodecyl sulfate, saponite, and mixtures thereof.

16. The controlled porous osmotic pump tablet according to claim 15, wherein the lubricant comprises magnesium stearate.

17. The controlled porous osmotic pump tablet according to claim 1, further comprising a thin film comprising the principal agent coated on the semipermeable membrane.

18. The controlled porous osmotic pump tablet according to claim 17, wherein the thin film comprises, by weight percents, 20-40% of the principal agent, 50-80% of a film-forming material, and 5-10% of a plasticizer, and the quantity of principal agent in the principal agent-comprising thin film is 10-20% of the quantity of principal agent in the core.

19. A controlled porous osmotic pump tablet without being drilled by using laser, comprising:
   (a) a core comprising, by weight percent, 25-50% of venlafaxine hydrochloride, 10-35% of a permeation enhancer, 20-40% of a permeation aid, and 0.5-1% of a lubricant;
   (b) a semipermeable membrane disposed over the core, the semipermeable membrane comprising pores and comprising, by weight percent, 50-70% of a film-forming material, 20-45% of a pore-forming agent forming the pores of the semipermeable membrane, and 3-10% of a plasticizer,
   wherein the semipermeable membrane is present in an amount of 10-35% by weight of the core, said pore-forming agent is selected from the group consisting of polyethylene glycol 2000-6000, hydroxypropyl cellulose, or both, and the film-foaming material is selected from the group consisting of cellulose acetate, ethyl cellulose, hydroxypropylmethyl cellulose, polyacrylic resin, and mixtures thereof; and, optionally,
   (c) a film coated on the semipermeable membrane, the film comprising, by weight percent, 20-40% of venlafaxine hydrochloride, 50-80% of a film-forming material, and 5-10% of a plasticizer,
   wherein the weight of venlafaxine hydrochloride in the film is 10-20% of the weight of venlafaxine hydrochloride in the core.

20. A process for preparing the controlled porous osmotic pump tablet without being drilled by using laser, comprising:
   (1) preparing a core by:
      (a) uniformly mixing venlafaxine hydrochloride, sodium chloride and microcrystalline cellulose;
      (b) granulating the resultant mixture;
      (c) tabletting the resultant granules upon uniformly mixing with microcrystalline cellulose and magnesium stearate;
   (2) preparing a semipermeable membrane comprising pores by: dissolving cellulose acetate, polyethylene glycol 6000 and dibutyl sebacate with a suitable solvent to obtain a first coating solution;
   (3) coating the core with the first coating solution in a coating machine;
   (4) volatizing any remaining solvent from the coated tablets to dryness to form the semipermeable membrane; and optionally,
   (5) preparing a second coating solution by: dissolving venlafaxine hydrochloride, hydroxypropylmethyl cellulose and polyethylene glycol 4000 with a suitable solvent;
   (6) coating the tablets of step (4) with the second coating solution; and
   (7) volatizing any remaining solvent from the coated tablets to dryness.

21. The process according to claim 20, further comprising (5) placing the semipermeable membrane-coated tablets in a coating machine, and (6) coating the tablets with a thin film coating solution.

22. The process according to claim 21, wherein the thin film coating solution comprises the principal agent.

23. The controlled porous osmotic pump tablet of claim 1, wherein the pores of the semipermeable membrane are continuous pores.

24. The controlled porous osmotic pump tablet of claim 1, wherein the principal agent is water soluble and permeable in the semipermeable membrane.

\* \* \* \* \*

UNITED STATES PATENT AND TRADEMARK OFFICE
CERTIFICATE OF CORRECTION

PATENT NO. : 8,703,193 B2  Page 1 of 1
APPLICATION NO. : 12/445690
DATED : April 22, 2014
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 665 days.

Signed and Sealed this

Twenty-ninth Day of September, 2015

Michelle K. Lee
*Director of the United States Patent and Trademark Office*